United States Patent

Reid et al.

[11] Patent Number: 6,005,964
[45] Date of Patent: *Dec. 21, 1999

[54] AUTOMATIC MACHINE VISION MICROSCOPE SLIDE INSPECTION SYSTEM AND METHOD

[75] Inventors: John F. Reid; John O'Brien, both of Champaign, Ill.

[73] Assignee: The Board of Trustees of the University of Illinois, Urbana, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/592,721

[22] Filed: Jan. 24, 1996

[51] Int. Cl.[6] .............................. G06K 9/00; G01N 21/76; A61B 6/02
[52] U.S. Cl. .......................... 382/133; 378/42; 435/40.5; 436/172
[58] Field of Search .............................. 250/461.2, 458.1, 250/461.1, 453.11; 348/79; 356/39, 335; 364/922; 382/128, 133, 134; 435/7.21, 7.22, 40.5, 4, 7, 1, 7.2, 7.23; 436/172, 63; 377/6; 600/476; 328/128–134, 270, 274–275; 378/6

[56] References Cited

U.S. PATENT DOCUMENTS

| | | | |
|---|---|---|---|
| 4,125,828 | 11/1978 | Resnick et al. | 382/134 |
| 4,199,748 | 4/1980 | Bacus | 382/134 |
| 4,263,010 | 4/1981 | Randolph | 23/23.09 |
| 4,376,839 | 3/1983 | Malin | 522/100 |
| 4,564,444 | 1/1986 | Hiraoka et al. | 210/96.1 |

(List continued on next page.)

FOREIGN PATENT DOCUMENTS

PCT/US92/ 01514  9/1992  WIPO .............................. G06K 9/00

OTHER PUBLICATIONS

"On Line Evaluation By Vision Systems In Bio–Technologies" by Antoine Grand d'Esnon et al., presented at the 1989 International Summer Meeting, American Society of Agricultural Engineers, Paper No. 89 7057, on Jun. 25–28, 1989.

"Recnet Developments in Process Sensors and Principles of Selection[1]" by J.F. Reid et al., Cereal Foods World, vol. 36, No. 4, pp. 356–362, dated Apr. 1991.

"A Vision–based System for Computer Control and Data Acquisition in fermentation Processes" by John F. Reid et al., presented at 38th Food Technology Conference, dated Mar. 2, 1992.

"Digital Image Analysis System for Determining Tissue–Blot Immunoassay Results for Ratoon Stunting Disease of Sugarcane" by J.M. Shine, Jr., et al., Plant Disease, vol. 77 No. 5, pp. 511–513 (May 1993).

(List continued on next page.)

Primary Examiner—Jon Chang
Assistant Examiner—Jayanti K. Patel
Attorney, Agent, or Firm—Greer, Burns & Crain, Ltd.

[57] ABSTRACT

A system for automatically detecting the presence of contaminants in samples. The system includes a microscope, controllable stage positioner for holding slides under the microscope, a computer for controlling the stage positioner and a digital camera to capture images through the microscope. The system scans microscope views of regions of a slide sample and provides the digital images to the computer. Image processing routines stored in the computer analyze the digital images and determine whether these images may contain certain contaminants by comparing the characteristics of the objects in the image with the known characteristics of the contaminants. The system also contemplates a method for automatically determining the presence of contaminants in samples including the steps of providing a microscope slide containing a sample, obtaining a plurality of digital microscope images of the sample, storing the digital images in a computer, automatically comparing characteristics of each digital image to characteristics of known contaminants and storing the results of the comparison.

7 Claims, 8 Drawing Sheets

U.S. PATENT DOCUMENTS

| | | | |
|---|---|---|---|
| 4,654,134 | 3/1987 | Morris et al. | 204/256 |
| 4,783,269 | 11/1988 | Baba et al. | 210/709 |
| 4,786,165 | 11/1988 | Yamamoto et al. | 356/23 |
| 4,888,703 | 12/1989 | Baba et la. | 364/496 |
| 5,006,231 | 4/1991 | Oblad et al. | 210/96.1 |
| 5,009,794 | 4/1991 | Wynn | 210/739 |
| 5,062,066 | 10/1991 | Scher et al. | 364/149 |
| 5,104,527 | 4/1992 | Clinkenbeard | 210/94 |
| 5,135,851 | 8/1992 | Kajander | 435/34 |
| 5,162,990 | 11/1992 | Odeyale et al. | 364/413.1 |
| 5,352,613 | 10/1994 | Tafas et al. | 436/63 |
| 5,422,428 | 6/1995 | McGuire et al. | 530/350 |
| 5,465,724 | 11/1995 | Sliwa, Jr. et al. | 128/662.03 |

OTHER PUBLICATIONS

"Knowledge–based Supervision and Control of Bioprocess with a Machine Vision–based Sensing System" by Jinlian Ren et al., Journal of Biotechnology 36 (1994) 25–34.

"A Prototype Neural Network Supervised Control System for *Bacillus thuringiensis* Fermentations" by Qin Zhang et al., Biotechnology and Bioengineering, vol. 43, pp. 483–489 (1994).

"Coupling a Machine Vision Sensor and a Neural Net Supervised Controller: Controlling Microbial Cultivations" by Qin Zhang et al., Journal of Biotechnology 1140 (1994) pp. 1–10.

"Automatic Pap Screening System Gets FDA Nod", Biophotonics International, dated Sep./Oct. 1995.

AUTOMATIC MACHINE VISION MICROSCOPE SLIDE INSPECTION SYSTEM AND METHOD

FIELD OF INVENTION

The present invention relates generally to systems and methods for automatic microscopy analysis, and, in particular, to a system and method for automatic machine vision detection of certain contaminants in samples on microscope slides.

BACKGROUND OF THE INVENTION

The presence of microscopic organisms in public drinking water is a threat to public health. Two particular pathogenic protozoa pose a significant threat, Giardia Lamblia and Cryptosporidium. Research conducted in 1991 showed the scope of the problem. This research revealed significant presence of these protozoa in the drinking water of several states and Canada. (Rose, J. B., C. P. Gerba and W. Jakubowski. 1991. Survey of Potable Water Supplies for Cryptosporidium and Giardia, Environmental Science and Technology. Vol. 225, no. 8, pp. 1393–1400; LeChevallier, M. W., W. D. Norton and R. G. Lee. 1991. Giardia and Cryptosporidium spp. in Filtered Drinking Water Supplies, Applied and Environmental Microbiology. Vol. 57, no. 9, pp. 2617–2621). In the spring of 1993, the presence of Cryptosporidium in Milwaukee's water supply caused over two dozen deaths. (Gurwitt, Rob. 1994. Something in the Water, Governing. Sept., 1994, pp. 32–38). 400,000 other people suffered from diarrhea, vomiting and intestinal cramps. During 1991 and 1992, 34 waterborne disease outbreaks were reported by the Center for Disease Control. Of these outbreaks, where a cause was found, 64% were associated with Giardia or Cryptosporidium. (Moore et al. 1994. Waterborne Disease in the United States, 1991 and 1992, Journal of the American Water Works Association. February pp. 87–99).

The Surface Water Treatment Rule (SWTR) specifies turbidity regulations for drinking water. The above-noted outbreaks recently caused the Environmental Protection Agency (EPA) to propose amendments to the SWTR. This enhanced rule (ESWTR) will provide additional protection against disease causing pathogens such as Cryptosporidium, Giardia and viruses. (EPA, Jul. 29, 1994. National Primary Drinking Water Regulations: Enhanced Surface Water Treatment Requirements; Proposed Rule, Federal Register, Vol. 59, No. 145). A proposed nation-wide monitoring program called the Information Collection Rule (ICR) will require microbial monitoring over a three year period. These requirements in the ICR are estimated to cost 1,725 water plants $11.8 million. (EPA, Feb. 10, 1994. Monitoring Requirements for Public Drinking Water Supplies; Proposed Rule, Federal Register, Vol. 59, No. 28). Results of the ICR will provide raw data for the determination of the improved regulations in the ESWTR. One regulation scenario projects an estimate of additional capital expenditures for domestic water utilities of $4.5 billion.

The occurrence of an outbreak from microbial pathogens might result from a malfunction of any water treatment system. The prevention of an outbreak could be accomplished through detection of microorganism presence in finished drinking water prior to distribution.

Under the current ICR, slide samples of drinking water are inspected using a microscope by an operator. Using current identification techniques, a microscope operator can process approximately 3–4 samples in a work week. Under EPA regulations, operators are restricted to four working hours at the microscope each work day. This limitation is enforced to prevent operator fatigue and bias in microorganism identification. Even under these limitations, the difficult nature of the required analysis subjects the inspection to human error and subjective bias.

Accordingly, it would be desirable to have an improved system and method for automatically detecting contaminants such as pathogenic protozoa in samples. Such a system and method would make inspection more efficient and accurate.

SUMMARY OF THE INVENTION

According to a first aspect of the present invention, a system for automatic detection of contaminants in samples, such as pathogenic protozoa in drinking water, is provided comprising a microscope with a camera attached, a computer which is connected to the camera so it can receive digital images of objects on a microscope slide, and an image processor in the computer for analyzing the digital images and detecting the possible presence of a contaminant in the slide sample.

According to a second aspect of the present invention, a system for automatic detection of contaminants in samples is provided comprising a microscope, a controllable stage positioner for holding and locating microscope slides under the microscope, a color camera connected to the microscope, a computer connected to the color camera and to the stage positioner, and an image processor for analyzing images taken by the color camera to detect the presence of contaminants in the sample. The computer is operable to receive images from the color camera of objects on a microscope slide and to control the stage positioner to control the position of the microscope slide under the microscope.

According to a third aspect of the present invention, a method for detecting the presence of pathogenic protozoa in water is provided, comprising steps of providing a microscope slide of a water sample, positioning the slide on a stage positioner under a microscope, scanning the slide to obtain a plurality of microscope images of different regions of the slide, providing the images to a computer, analyzing the image with a routine on the computer to determine whether pathogenic protozoa are present in the sample and storing the results of this analysis.

DETAILED DESCRIPTION OF THE PRESENTLY PREFERRED EMBODIMENTS

Figure 1:
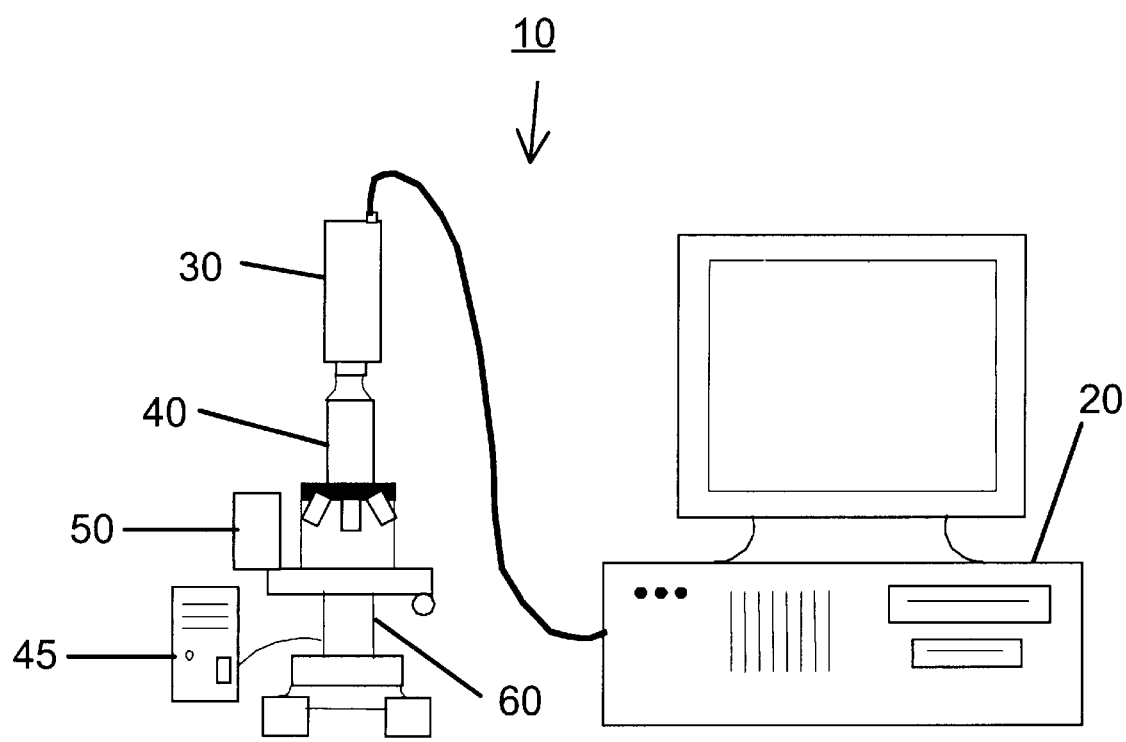
FIG. 1 is a block diagram of an automatic machine vision microscope slide inspection system made in accordance with the preferred embodiments of the present invention.

FIG. 1 schematically illustrates an automatic microscope slide inspection system 10 made in accordance with the presently preferred embodiments of the invention. The system 10 includes a computer 20, a color camera 30, a microscope 40 with fluorescence and differential interference contrast capability, a slide feeding mechanism 50 and a computer controlled stage positioner 60. The microscope 40 includes a fluorescent mercury light source. The light source can either have a mercury burner device 45 that is separate from the microscope (as shown in FIG. 1) and that is connected to a light on the microscope (not shown) or be completely built in the housing of the microscope.

The color camera 30 is coupled to the microscope 40 and is operable to obtain images of the spectral reflectance of objects on a microscope slide on the stage positioner 60. The stage positioner 60 operates to hold and locate slides received from the slide feeding mechanism 50 under the lens of the microscope 40. In the preferred embodiments, the microscope 40 has conventional controls, such as focus and resolution, that are controlled by the computer 20.

The camera 30 is also operatively associated with the computer 20 so that images obtained through the microscope 40 can be received, stored and manipulated by the computer 20. Also, in the preferred embodiments, the computer 20 includes a video image processing board (not shown). This board is operable to convert digitize video images received from the camera 30. Alternatively, the camera 30 can be operable to digitize the image before sending it to the computer 20. In the preferred embodiments, the computer 20 also includes an analog to digital and digital to analog converter (not shown). This converter allows the computer to control the microscope 40 and the stage positioner 60. The computer 20 also includes Random Access Memory ("RAM"), a storage device such as a hard disk drive, a keyboard, and a monitor. The stage positioner 60 is operatively associated with the computer 20 so that the exact position of the slide being viewed by the microscope can be controlled by the computer 20.

The computer 20 contains software that enables the conversion of the data received from the camera 30 into a set of morphometric or photometric features regarding the content of the image. The computer 20 also has image processing software that analyzes and interprets the detected image to determine whether certain pathogenic protozoa are present. There are presently at least two alternative preferred embodiments of the invention. The second alternative preferred embodiment uses additional software to analyze the detected image. The operation of the software in each of the presently preferred embodiments is discussed in more detail below.

In the presently preferred embodiments, the microscope 40 is Olympus Corporation's Model No. BMAX-60 microscope. This model includes a built-in mercury light source. Alternatively, Olympus Corporation's Model No. BH2 microscope can be used in conjunction with a mercury light source also manufactured by Olympus. Olympus Corporation is located at 4- Nevada Drive, Lake Success, N.Y. 11042. As those skilled in the art will appreciate, commercially available microscopes other than those listed here may be utilized. For example, suitable microscopes are offered by Nikon Inc., Instrument Group, 623 Stewart Ave., Garden City, N.Y. 11530.

In the presently preferred embodiments, the stage positioner 60 comprises the Prior Scientific Model No. H101, manufactured by Prior Scientific, 80 Reservoir Park Drive, Rockland, Mass. 02370. The camera 30 is preferably a color CCD camera with at least 512 by 512 pixel resolution. Such cameras are readily available from many different manufacturers, such as Sony, Kodak and Photometrics. The computer 20 is preferably a Gateway 2000 computer. The presently preferred image processing board is the Matrox Meteor board, manufactured by Matrox Electronic Systems, Ltd., 1025 St. Regis Blvd., Dorvel Quebec CANADA. As those skilled in the art will appreciate, commercially available hardware other than that discussed above may be utilized without departing from the spirit and essential characteristics of the present invention.

In the presently preferred embodiments of the invention, the system 10 operates to inspect slides prepared from drinking water samples to detect the presence of contaminants. In the presently preferred embodiments, the contaminants to be detected are pathogenic protozoa. In particular, the preferred embodiments detect two different microorganisms—Giardia Lamblia and Cryptosporidium. The preferred embodiments are used to analyze the same type of slide samples of drinking water that are analyzed manually under the current EPA technique—namely, dry mounted slide samples that include an immunofluorescent antibody marker.

Figure 2:
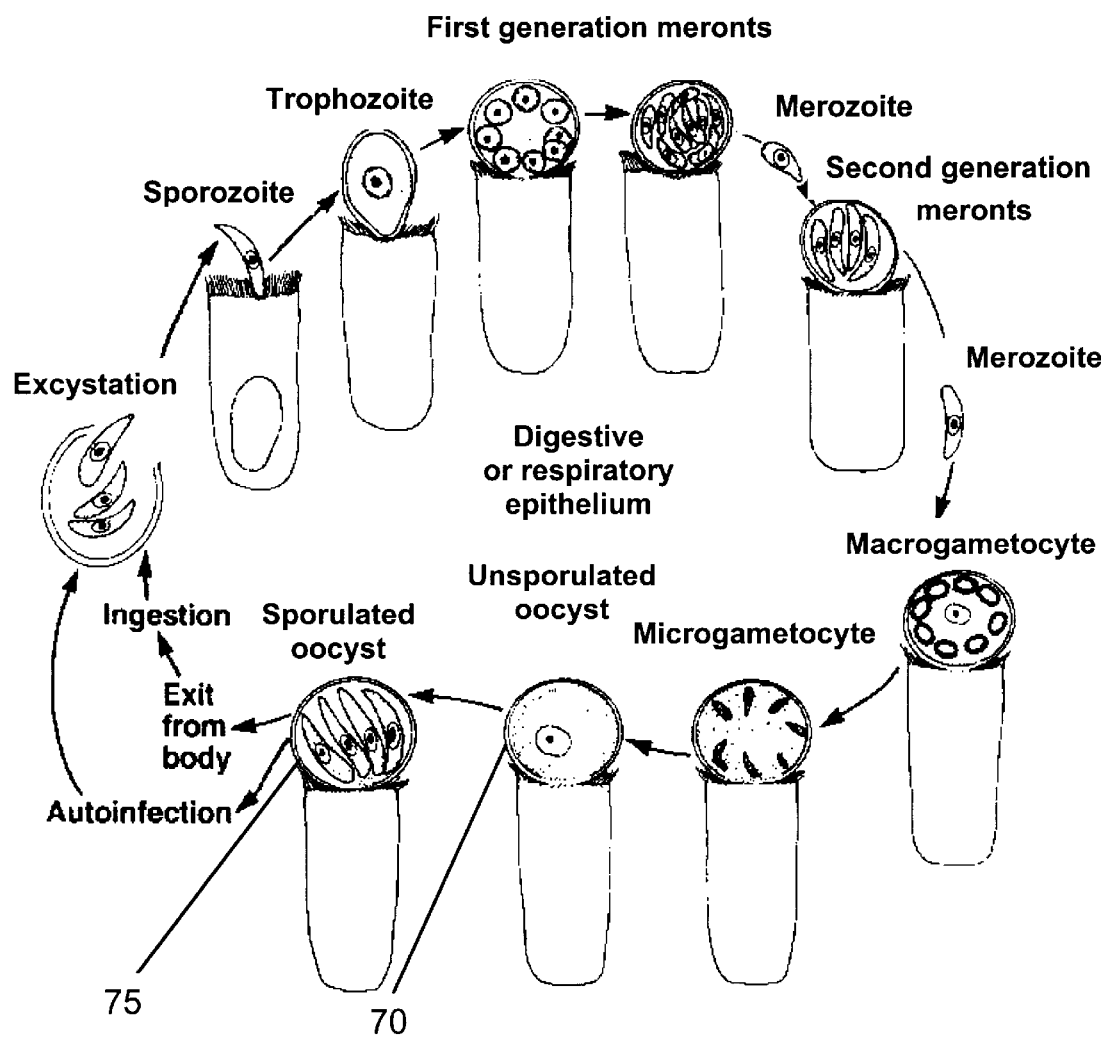
FIG. 2 is a diagram illustrating of the life cycle of a Cryptosporidium microorganism.
Figure 3:
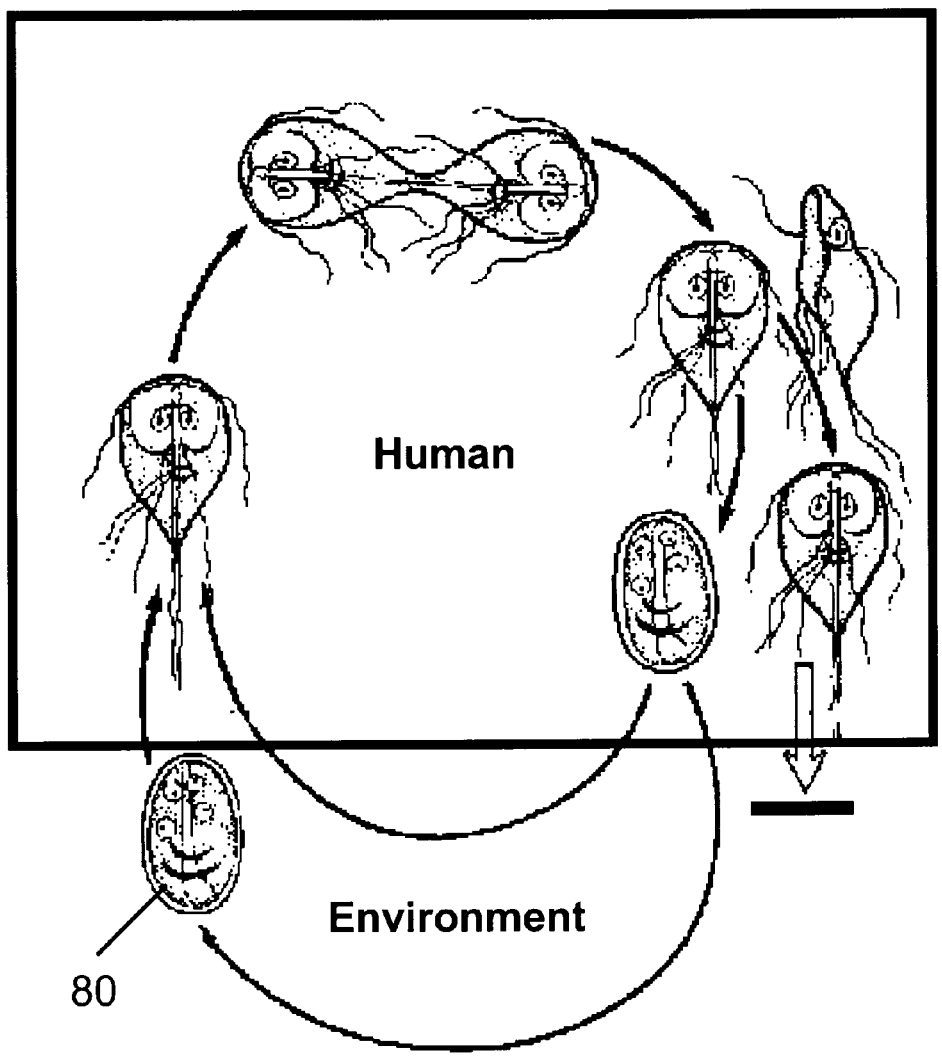
FIG. 3 is a diagram illustrating the life cycle of a Giardia Lamblia microorganism.
Figure 4:
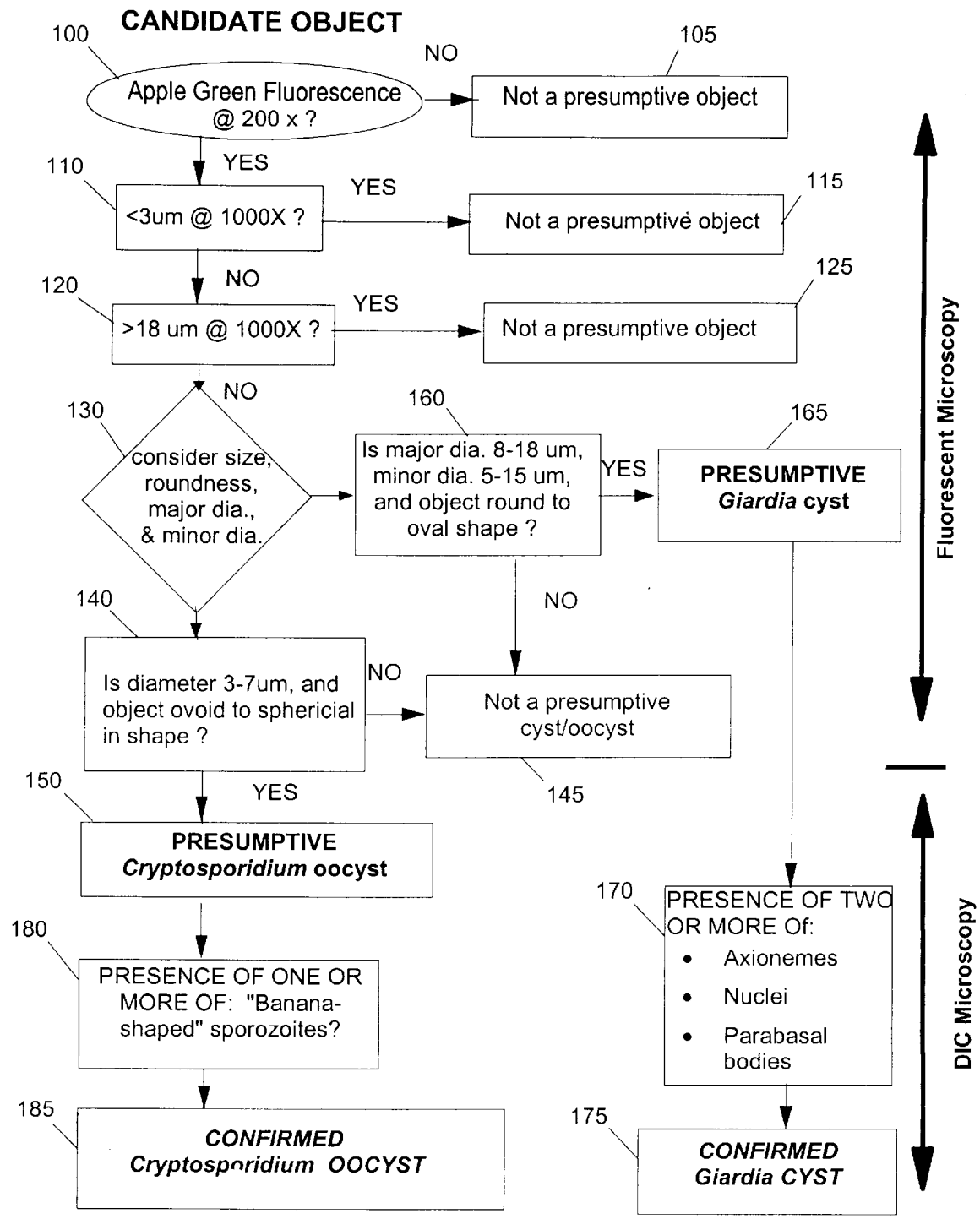
FIG. 4 is a flow chart outlining the steps of the EPA procedure for detecting Cryptosporidium and Giardia Lamblia in drinking water.

FIGS. 2 and 3 show the life cycles of Cryptosporidium and Giardia Lamblia, respectively. The presence in drinking water of Cryptosporidium in its oocyst stages 70 and 75 is dangerous to humans. Similarly, Giardia Lamblia is considered dangerous in drinking water in its cyst stage 80. The EPA has established a procedure for detecting the presence of these pathogenic protozoa at their oocyst and cyst stages in drinking water. FIG. 4 is a flow chart showing the steps of this procedure. The EPA detection procedure is presently conducted manually by a microscope operator.

The EPA procedure requires two different types of microscopy tests. The first is fluorescent microscopy. This type of microscopy involves putting a fluorescent marker, such as an antibody, into the sample. The physical dimensions of Cryptosporidium and Giardia Lamblia in the oocyst and cyst stages are known. Cryptosporidium oocysts are ovoid to spherical, ranging from 3 to 7 $\mu$m in diameter. Giardia Lamblia are round to oval in shape and are 8 to 18 $\mu$m long by 5 to 15 $\mu$m wide. These external dimensions can be recognized using fluorescent microscopy as shown in the first part of FIG. 4. It is known that the oocysts and cysts in question emit an "apple green" fluorescence. Fluorescent microscopy can be used on the samples and the distribution of color content in a candidate object can be evaluated for its correlation to the hue distribution of known cysts or oocysts fluorescing in response to a mercury light source.

As shown at steps 100 and 105 in FIG. 4, if no apple green fluorescence is detected at 200 times magnification, then it is known that no cysts or oocysts are present. If apple green fluorescence is detected, examining the physical dimensions of the objects emitting apple green fluorescence allows one to determine whether the object is possibly a Cryptosporidium oocyst or a Giardia cyst. If a dimension is less than 3 $\mu$m, the smallest dimension of known oocysts and cysts, then the object can be ruled out (steps 110 and 115). Similarly, if a dimension is greater than 18 $\mu$m, the largest dimension of known oocysts and cysts, the object can be ruled out (steps 120 and 125). If the object cannot be ruled out, shape of the object is to be considered. If the object is ovoid to spherical in shape and has a diameter between 3 and 7 μm, it may possibly be a Cryptosporidium oocyst (steps 130, 140 and 150). If it is ovoid to spherical and has a diameter less than 3 μm or greater than 7 μm, then it can be ruled out (steps 130, 140 and 145). If the object is round to oval shape and has a major diameter between 8 and 18 μm and a minor diameter between 5 and 15 μm, it may possibly be a Giardia cyst (steps 130, 160 and 165). However, if it is round to oval and does not fall within these dimension ranges, it can be ruled out (steps 130, 160 and 145).

The second part of the EPA procedure is used to confirm whether possible oocysts and cysts detected by the first part are actually oocysts or cysts. This part utilizes differential interference contrast microscopy to detect the presence of internal organelles typical of each protozoa. Giardia Lamblia cysts are confirmed with the identification of two or more of identifying structures such as axionemes, nuclei and parabasal bodies (steps 170 and 175). Cryptosporidium oocysts are confirmed by checking for the presence of one or more banana shaped sporozoites (steps 180 and 185).

Figure 5:
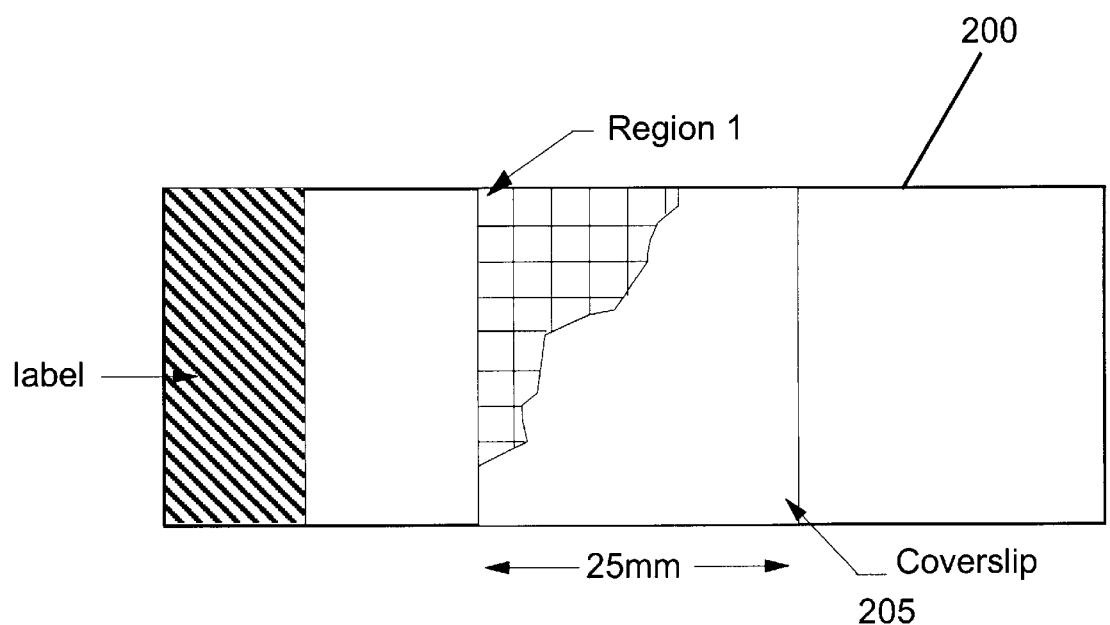
FIG. 5 is a plan view of a slide illustrating the manner in which the image processing software of the presently preferred embodiments divides the coverslip of a slide into regions.

In one presently preferred embodiment of the present invention, system 10 of FIG. 1 is operable to automatically perform the fluorescent microscopy procedures illustrated in FIG. 4 at steps 100–165. Prior to performing an analysis of slide samples using system 10, the microscope 40 and camera 30 should be calibrated. This calibration should include a calibration for spatial determination and distortion to convert the image received to coordinates on the coverslip of the slide. As shown in FIG. 5, the image processing software in the computer 20 treats the coverslip region 205 of the slide 200 as if it is divided into a grid of rectangular shaped regions. In the first presently preferred embodiment, this grid consists of 455 by 338 μm rectangles. On a standard 25 mm by 25 mm coverslip and with a resolution of 0.6 by 0.7 μm, the grid comprises a 55 by 74 array of regions. As known in the art, a hemocytometer can be used to calibrate the camera 30 to the specific grid layout to be used. Also, the camera 30 should be calibrated for hue determination using a sample of the fluorescent labelling reagent to be used. In the preferred embodiments, the labelling reagent is fluorescein isothiocyanate (FITC). As known in the art, other labelling reagents such as 4',6-diamidino-2-phenylindole (DAPI) or propidium iodide (PI) may be used. These calibration techniques are well known in the art.

After the system is calibrated, the system 10 of FIG. 1 is operable to automatically analyze slide samples. In the first presently preferred embodiment, the slide feeding mechanism 50 places a dry mounted slide of a drinking water sample on the stage positioner 60. The sample contains the immunofluorescent antibody used in the EPA procedure (FITC). Prior to analyzing the slide, the initial zero reference location on the coverslip (the first region to be analyzed) is determined. This is done using standard edge detection techniques well known in the art and can be performed by using commercially available image processing software such as the Image Pro Plus from Media Cybernetics (8484 Georgia Ave., Silver Spring, Md. 20910), the Matrox Inspector from Matrox Electronic Systems, Ltd. (1025 St. Regis Blvd., Dorvel Quebec Canada), or the Global Lab Image software from Data Translation (100 Locke Drive, Harlboro, Mass. 01752-1192). Edge detection techniques are discussed in commercially available references such as Gonzalez, R. C. and R. E. Woods, 1992, *Digital Image Processing*, Addison-Wesley, New York; Russ, J. C., 1995, *The Image Processing Handbook*, CRC. Press, Boca Raton; Myler, H. R. and A. R. Weeks, 1993, *The Pocket Handbook of Image Processing Algorithms In C*, Prentice Hall, Englewood Cliffs, N.J.; and Myler, H. R. and A. R. Weeks, 1993, *Computer Imaging Recipes In C*, Prentice Hall, Englewood Cliffs, N.J.

Figure 7:
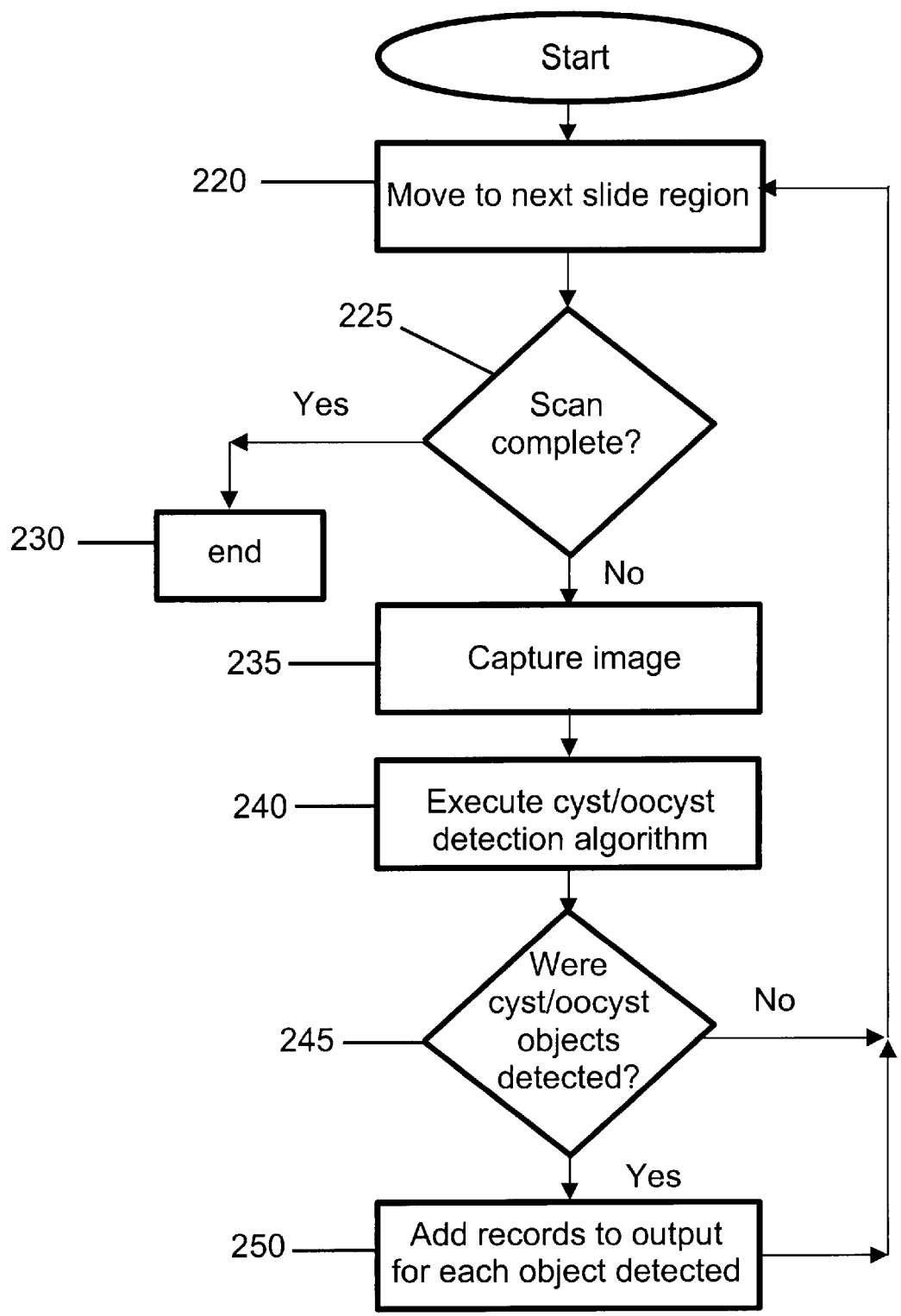
FIG. 7 is a flow chart outlining the steps performed by the controller software program to be executed on the system depicted in FIG. 1.

FIG. 7 shows a flow chart outlining the steps performed by the controller software of this embodiment once a slide is placed on the stage positioner 60 and after its zero reference location is determined. At step 220, the controller software in computer 20 instructs the stage positioner 60 to move so that the next region to be scanned is under the microscope 40. The first region to be scanned is the zero reference location. As shown at steps 225 and 230, if there are no more regions left to be scanned, the analysis is complete. Otherwise, at step 235, the camera 30 takes an image of the region through the microscope 40 at 200 times magnification using fluorescence microscopy (using a mercury light source). Preferably, the camera 30 divides each image into an array of at least 512×512 pixels. This image is converted by the image processing board in the computer 20 into a digital image and is preferably stored in the RAM of the computer 20. If necessary, this image may also be stored in a cache memory location of the hard disk drive of the computer 20.

Next, at step 240, the image processor routine is called to detect whether Cryptosporidium oocysts or Giardia Lamblia cysts are potentially or presumptively present in the image. This routine is described in more detail below.

If the image processor routine reveals any presumptive cysts or oocysts, the location of each object, the object data and the image of the region containing the object are saved to the hard disk drive of the computer 20, as shown at steps 245 and 250. Otherwise, the controller software returns to step 220 and the above described process is repeated.

The location of each object is identified using X, Y and Z coordinates. The Z coordinate represents the distance of the object from the top surface of the slide. This is determined from depth of the stage positioner 60 and the focal point of the microscope 40. The object data stored can be any of the statistical data relating to the object generated by the connected component/blob/particle analysis used by the image processor routine. In the presently preferred embodiments, the object data stored includes at least the maximum and minimum diameters of the object, a measurement of the perimeter of the object, the mean hue measurement value for the pixels in the object, the variation of the hue measurement values, and a measure of the sphericity of the object (roundness). After this information is stored, the controller software returns to step 220 and the above described process is repeated.

Figure 6:
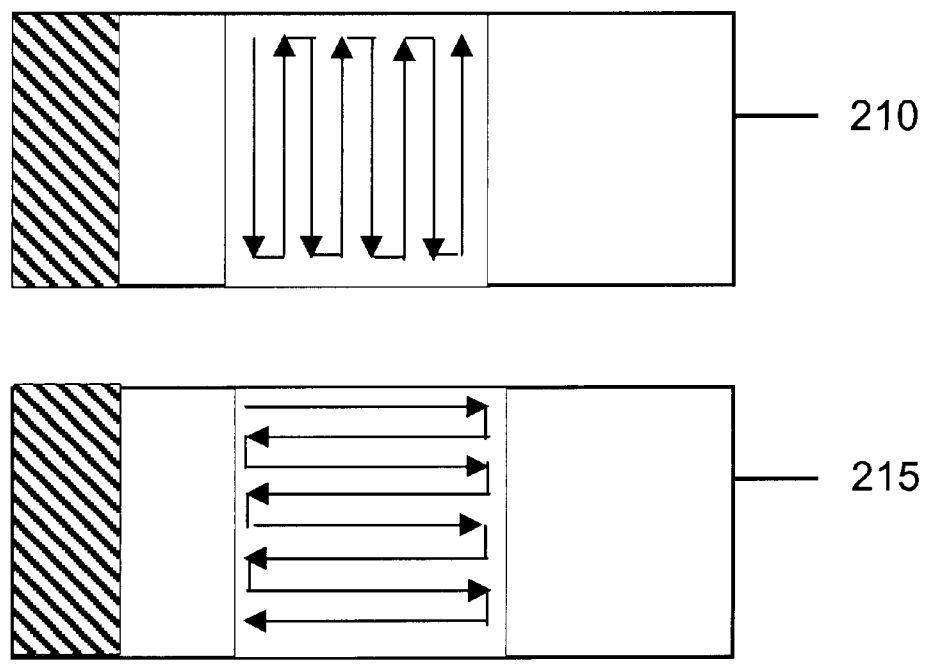
FIG. 6 is a plan view of two slides illustrating the preferred method of scanning to be used in the presently preferred embodiments.

The EPA procedure specifies that two different scanning patterns be used with each sample. Each of these scanning patterns is illustrated in FIG. 6. As shown by the arrows on slide 210, one pattern proceeds from column to column. As shown by the arrows on slide 215, the other pattern proceeds from row to row. In the presently preferred embodiments, the controller software performs both of these scanning patterns on each sample. However, if the microscope and stage positioner are accurate enough, only one scanning pattern may be necessary.

Figure 8:
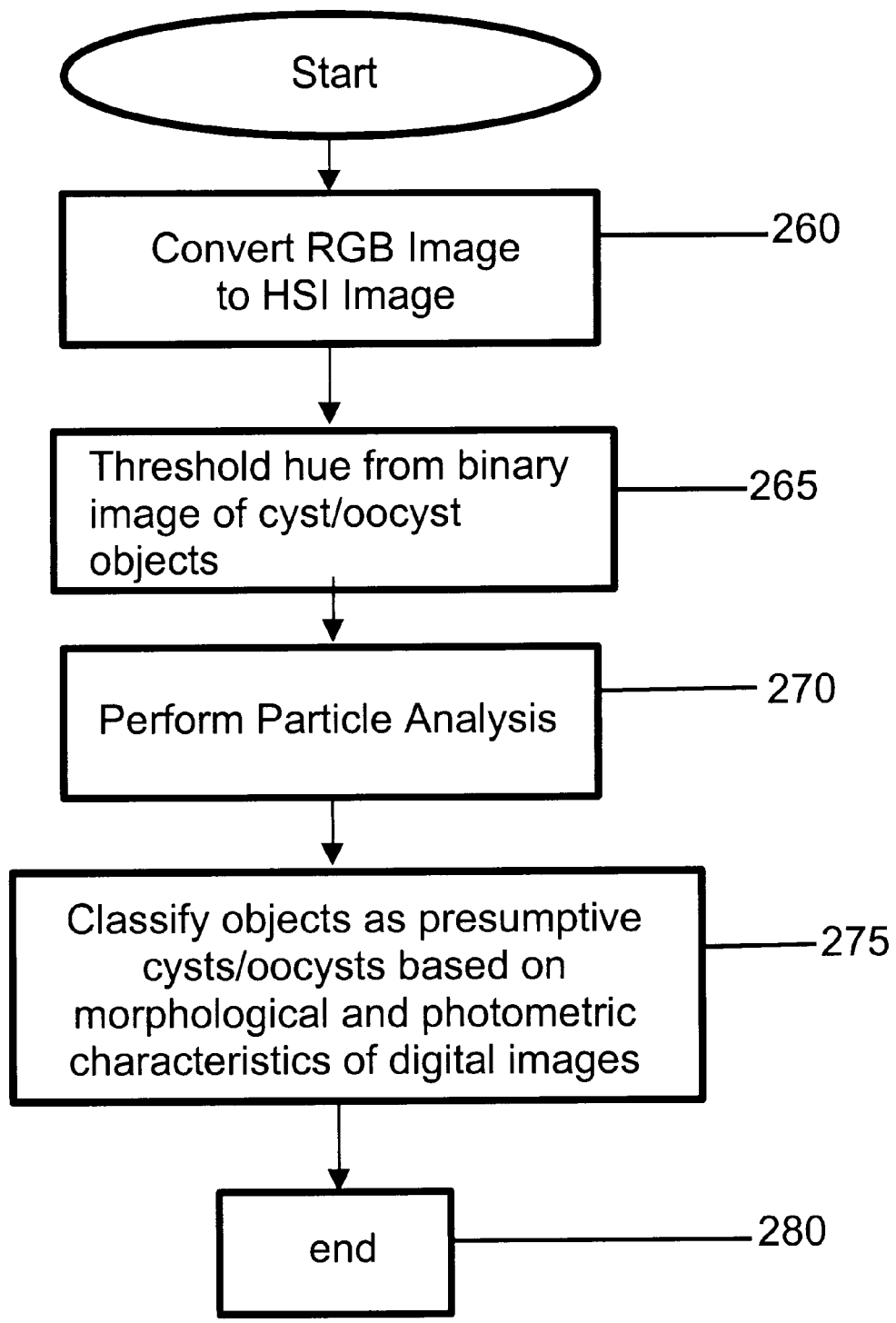
FIG. 8 is a flow chart outlining the steps performed by the image processor routine after it is called by the controller software program shown in FIG. 7.

FIG. 8 shows a flow chart outlining the steps performed by the image processor routine. This routine is called by the controller software described above. First, at step 260, the image processor routine performs a Red-Green-Blue (RGB) to Hue Saturation Intensity (HSI) conversion of the image. This conversion is well known in the art and can be performed using commercially available software such as the Image Pro Plus or the Matrox Inspector. This conversion causes each pixel in the image to be assigned an independent measurement of hue. RGB to HSI conversion techniques are discussed in commercially available references such as those discussed above with respect to edge detection.

Next, at step 265, the image processor routine compares the hue measurement of each pixel to the threshold upper and lower limits of the known hue of the contaminant at issue (in the preferred embodiments, this is the "apple green" hue) and converts the image to a binary image. In this binary image, those pixels having a hue measurement greater than the upper threshold or lower than the lower threshold are assigned the value 0, while the other pixels retain their hue measurement value. Such a threshold comparison is known in the art and can be performed using commercially available software such as the Image Pro Plus, the Matrox Inspector or the Global Lab Image software. Thresholding techniques are also discussed in commercially available references such as those discussed above.

Next, at steps 270 and 275, the image processor routine performs a particle/connected component/blob analysis of the binary image to determine if any of the apple green objects found are of the proper size and shape to be considered potential or presumptive Cryptosporidium oocysts or Giardia Lamblia cysts. This type of analysis is well known in the art and can be performed using commercially available software such as the Matrox Inspector or Global Lab Image. Connected component, particle or blob analysis techniques are discussed in commercially available references such as Gonzalez, R. C. and R. E. Woods, 1992, *Digital Image Processing,* Addison-Wesley, New York and Russ, J. C., 1995, *The Image Processing Handbook,* C.R.C. Press, Boca Raton. Next, at step 280, the routine ends and returns to the controller software as shown at step 245 of FIG. 7.

After the scanning caused by the controller software has been completed at step 230 of FIG. 7, software in computer 20 preferably displays a list of all presumptive cyst/oocyst locations on the computer monitor. This list is preferably rated according to the size of the objects and the statistical variation of the hue of the objects. Also, the software preferably allows an operator to select objects he/she would wish to examine to manually perform steps 170–185 of the EPA procedure shown in FIG. 4. After the user selects an object, the software preferably retrieves the saved image and displays it on the monitor with the perimeter of the presumptive objects highlighted in a distinctive color. Preferably, the software will also cause the stage positioner 60 to move so that the region containing the selected object is under the microscope 40. The operator can then analyze the presumptive object to determine whether it is in fact a cyst or oocyst. If so, the operator can mark the object as confirmed. If the operator determines that a presumptive object is not a cyst or oocyst, he can prompt the software to delete that record and its associated image from the record saved on the hard disk drive of computer 20. These steps can be repeated until the operator has evaluated all prospective regions.

Preferably, the system 10 also includes a color printer (not shown) coupled to the computer 20. Such a printer could be used by an operator to print those images that contain contaminants. Also, the software described above is preferably controllable by a user via an interface that includes pull down menus.

This system provides significant benefits over the present manual method. Using the system 10, an entire slide can be scanned and analyzed in less than six minutes. After this analysis, an operator will be directed to those images that potentially contain cysts or oocysts. When done manually, it takes at least one hour to analyze a single slide using fluorescent microscopy.

In another preferred embodiment of the present invention, the system 10 of FIG. 1 is also operable to automatically perform the differential interference contrast microscopy procedures illustrated in FIG. 4 at steps 170–185 to confirm the presence of cysts or oocysts. In this embodiment, the same steps shown in FIGS. 7 and 8 are performed. However, rather than prompting the operator to manually confirm whether the presumptive locations are actually cysts or oocysts, this embodiment includes software to perform this confirmation automatically. In this second preferred embodiment, the camera 30 should also be calibrated for the intensity of the light source. Also, after the presumptive analysis is complete, the camera 30 should be recalibrated for spatial determination and distortion because the confirmational analysis will use the microscope at 1000 times magnification.

The confirmational analysis routine of this second preferred embodiment will preferably work as follows. First, the routine causes the stage positioner 60 to move to the first presumptive cyst/oocyst location. Then, by controlling the depth of the stage positioner 60, the routine will cause the camera 30 to capture a series of images at different focal planes through the microscope 40 using differential interference contrast (DIC) microscopy at 1000 times magnification. These images of different layers of the presumptive object are saved.

Next, standard image processing techniques are used to identify high contrast features found in the layers of images. The routine classifies these features as axoneme, nuclei, parabasal bodies or spoorzoites based on the known characteristics of these internal organelles.

The routine then determines whether the presumptive object is actually a cyst or oocyst by using an artificial intelligence classification algorithm, such as a neural network or fuzzy logic, with a database containing characteristics of internal structures of known Cryptosporidium and Giardia Lamblia samples.

Next, the confirmational analysis routine causes the stage positioner 60 to move to the next presumptive location and the above-described steps are repeated until all presumptive locations have been analyzed. After the analysis is complete, a report listing all presumptive and confirmed cysts/oocysts is displayed. Preferably, in this embodiment a similar interrogation routine to the one described above will allow the operator to easily look at each presumptive or confirmed location.

The invention may be embodied in other forms than those specifically disclosed herein without departing from its spirit or essential characteristics. The described embodiments are to be considered in all respects as illustrative and not restrictive. The scope of the invention is commensurate with the appended claims and all equivalents rather than the foregoing description.

We claim:

1. A microscope slide inspection system for examining a sample, the system comprising:

means for obtaining a digital image of the sample;

means for performing a fluorescence microscopy analysis of the digital image to determine if an intensity threshold is crossed in one or more regions of the digital image indicating one or more objects of potential interest;

means for performing a size analysis of each of said one or more regions in which the intensity threshold is crossed to determine a spatial characteristic of any object of potential interest identified by said means for performing a fluorescence microscopy analysis;

means for declaring a presumptive result for any object of potential interest having a spatial characteristic exceeding a spatial threshold;

means for performing a differential interference contrast analysis of each object of potential interest for which a presumptive result has been declared and declaring a positive result for any presumptive result associated with an object of potential interest having predetermined contrast characteristics.

2. The system of claim 1 wherein a microscope performs the fluorescence microscopy analysis.

3. The system of claim 2 wherein the microscope is operable to perform differential interference contrast microscopy.

4. The system according to claim 1, wherein said intensity threshold is a hue intensity threshold.

5. The system according to claim 4, wherein said hue intensity threshold is set to detect pathogenic protozoa as said objects of potential interest.

6. The system according to claim 5, wherein said means for performing a fluorescence microscopy analysis identifies potential pathogenic protozoa of interest by comparing hue content distribution in said one or more regions of the digital image to known pathogenic protozoa hue distributions.

7. The system according to claim 1, wherein said means for obtaining a digital image of the sample obtains an image having a plurality of regions and sub-regions and said means for performing a fluorescence microscopy analysis analyzes said subregions individually and sequentially to identify any objects of potential interest in each of said sub-regions.

* * * * *

UNITED STATES PATENT AND TRADEMARK OFFICE
CERTIFICATE OF CORRECTION

PATENT NO.   : 6,005,964
DATED        : December 21, 1999
INVENTOR(S)  : Reid et al.

It is certified that error appears in the above-identified patent and that said Letters Patent is hereby corrected as shown below:

Column 1, line 5, insert new paragraph --This invention was made with Government support under Grant No. AG93-388420-8802 awarded by the USDA. The Government has certain rights in the invention--.

Signed and Sealed this

Seventh Day of November, 2000

*Attest:*

Q. TODD DICKINSON

*Attesting Officer*    *Director of Patents and Trademarks*